United States Patent [19]
Malachowski

[11] 3,995,030
[45] Nov. 30, 1976

[54] COMPOSITION AND METHOD FOR TREATING ARTHRITIS
[75] Inventor: Henry Malachowski, Wilton, Conn.
[73] Assignee: Robert Daniels & Company, Inc., Moonachie, N.J.
[22] Filed: Jan. 6, 1971
[21] Appl. No.: 104,502

[52] U.S. Cl. .............................. 424/127; 424/128; 424/167
[51] Int. Cl.² ................. A61K 31/00; A61K 33/00; A61K 33/42
[58] Field of Search ..................................... 424/167

[56] References Cited
UNITED STATES PATENTS
3,657,423  4/1972  Yacowitz .............................. 424/127

*Primary Examiner*—Sam Rosen
*Attorney, Agent, or Firm*—Fidelman, Wolffe & Waldron

[57] ABSTRACT

This invention relates to usage of the ignition residue of anthracite coal to treat arthritis.

9 Claims, No Drawings

COMPOSITION AND METHOD FOR TREATING ARTHRITIS

This invention relates to the treatment of arthritis, and in particular to a mineral composition which is of value in the treatment of arthritis, (including osteoarthritis, osteoarthrosis, and polyarthritis of unknown etiology).

Briefly stated, the therepeutic composition of the present invention consists of the ignition residue of anthracite coal.

This residue, in finely divided form, can be administered orally at dosage rates of up to 100 milligrams per kilogram of body weight.

Animal test studies at higher concentrations than 100 mg/kg of body weight indicate that the anthracite ignition residue is non-toxic and does not appear to affect detrimentally normal body functions.

Coal, as such, is a well known article of commerce mined and sold annually in the millions of tons all over the world. The nature of coal has been investigated at length, and studied efforts have been made to classify the various coals mined world-wide according to the properties of greatest interest to purchasers so that the users of one type or another may purchase a reasonably consistent commodity product. A well known classification system of coals pertinent to this invention is classification of coal according to rank into anthracite, bituminous, sub-bituminous and lignite, with each of the above classes of coal having several sub-groups therein. The ignition residue composition of the present invention is specifically derived from that class of coals generally known as anthracite and includes within this sense the several sub-groups of anthracitic coals known as meta-anthracite, anthracite and semi-anthracite. Characteristically, all of these anthracite coals are low volatile matter — high carbon content coals which are non-agglomerating. The limits generally given for the sub-group known as semi-anthracite (the anthracite having the lowest fixed carbon content and greatest volatile matter content) is a range of 86–92% for fixed carbon and 8–14% for volatile matter, all on a dry basis. Importantly, the semi-anthracite must be non-agglomerating. If a particular coal having about 86% fixed carbon, does agglomerate on heating, then it is classified as a low-volatile bituminous coal. The range given for anthracite is 92–98% fixed carbon 2–8% volatile, that for meta-anthracite is 98–100% fixed carbon, 0.–2% volatile matter.

To repeat, the compositions of the present invention are derived from anthracitic coals, preferably from the anthracite sub-group. Specifically, the compositions of the present invention constitute the ignition product thereof, the ash so to speak. Characteristically, the ash from commercial anthracite is 10% or more and is largely a non-clinker type of material. The present ignition product is prepared by controlled ignition at a temperature of about 1800°–2000° F. through heating an appropriate quantity of the coal, e.g., 50 pounds, to a temperature of 1800°–2000° F. in an open to air gas-fired commercial oven. The coal ignites during the heating cycle and burns to an ash. The ignition residue is collected and screened to remove those particles in excess of about ¼ inch in diameter, with the oversized particles being rejected. The screened ash may then be processed through a granulator to obtain the finely divided particles, e.g., 200 mesh and finer, which constitutes a preferred form of the composition of the present invention. If desired, the ground product may be dried (in a drying oven at 80° C. for a one-hour period) to remove any moisture which may have been taken up from the ambient atmosphere, before encapsulating, compressing into boluses, or admixing with an animal food substance.

Anthracite coal is a widely dispersed material of somewhat diverse properties (although not as diverse as exists in bituminous coals). Therefore, it may be surprising that the somewhat diverse materials all identifiable as anthracite coal will yield ignition residues having anti-arthritic properties, yet such seems to be true, at least insofar as can be determined through open market purchases of anthracite coal from diverse sources. If, it should ultimately be determined that not all anthracite ignition residues are pharmacologically active, the probable reason for the apparent universality of the anti-arthritic properties is that only those seams producing the pharmacologically active ignition residue are mined commercially at this time. For more than a generation, the anthracite mining industry has been in an ever-declining state with less and less anthracite mined year by year, until the industry appears nearly moribund. Only a few mines are in commercial operation in the United States. Be that as it may, the ignition residues of anthracite obtained from several sources all exhibit a beneficial pharmacologic effect on arthritis and it is therefore believed that this property is generic to anthracite.

The following specific example will serve to illustrate preparation of the anthracite coal ignition residue of the present invention:

Fifty pounds of pea-sized anthracite coal is spread thinly on the hearth of an open gas-fired commercial oven and the oven heated to a temperature in the range of 1800° to 2000° F and maintained in that temperature range (by control of the gas) until the coal has been reduced to an ash (approximately one hour). During this heating cycle, the anthracite ignites and can be seen to burn, being reduced ultimately to an almost carbon-free ash. The ignition residue weighing about eight pounds was collected, then screened through a No. 12 mesh screen to remove oversized particles. Thereafter, the screened residue was granulated to 200 mesh and finer. The finely divided product was placed in a drying oven at 80° C. for an additional one-hour period to insure a moisture free state and packaged in 50 mg, 100mg, 200 mg, 2,500 mg and 5,000 mg quantities in gelatin capsules, and 2,500 mg and 5,000 mg quantities compressed into bolus form.

The following table provides the analytic results of two representative anthracite ignition products, and also average values for a greater number of ignition residue runs.

TABLE

|  | Sample A-109 | Sample B-110 | General Range All Samples |
|---|---|---|---|
| $SiO_2$ | 44.36% | 45.70% | 42 – 48% |
| $Fe_2O$ | 6.00% | 6.00% | 5 – 8% |
| MgO | 0.90% | 0.80% | 0.75 – 1.0% |

TABLE-continued

| | Sample A-109 | Sample B-110 | General Range All Samples |
|---|---|---|---|
| $K_2O$ | 1.20% | 1.25% | 1.0 – 1.5% |
| ZnO | 0.08% | 0.07% | 0.05 – 0.10% |
| $Al_2O_3$ | 33.70% | 32.90% | 30 – 35% |
| CaO | 1.10% | 1.11% | 0.75 – 1.25% |
| $Na_2O$ | 1.20% | 1.15% | 1.0 – 1.25% |
| CuO | 0.30% | 0.33% | 0.2 – 0.4% |
| $Li_2O$ | 0.05% | 0.08% | 0.03 – 0.1% |
| $B_2O_5$ | 0.30% | 0.25% | 0.2 – 0.4% |
| Carbon total | 3.0% | Carbon total 2.3% | |
| Carbon as $CO_3$ | 4.20% | Carbon as $CO_3$ | 3.50 (0.6%C) |
| Free Carbon | 2.20% | Free Carbon | 1.70% |
| $H_2O$ | 3.50% | $H_2O$ | 3.50% |
| TOTAL | 99.09% | TOTAl | 98.34% |
| | | General Range All Samples | |
| | | Carbon total | 2. – 3.5% |
| | | Carbon as $CO_3$ | 2 – 5% |
| | | Free Carbon | 1 – 4% |
| | | $H_2O$ | 3 – 4% |

While it may offer reasonable to assume that not all of the ingredients present in the anthracite ignition residue are required for the anti-arthritic activity, considerable efforts to date have been unable to elicit the ingredient, ingredients or the form of ingredient to which pharmacological activity may be attributed.

To repeat, oral administration of the anthracite coal residue in dosages (daily) of up to 100 mg/kg of body weight relieves arthritic symptoms. Very little more can be said, the mechanism is completely unknown. In addition arthritis, in its many forms including rheumatism, human or animal, can result from an overwhelmingly large number of known causes. Often, the etiology of the disease is unknown, or at least cannot be determined with any degree of certainty. Perhaps more than is usual, the clinical judgment of the physician or veterinarian attending the case must determine whether the anthracite residue should be employed to treat a particular patient or animal. Oral administration of the anthracite residue cannot be expected to produce results for arthritic conditions associated with known infectious agents, and the physician or veterinarian may be expected to appreciate the limitations inherent in treatment with a mineral medicament. However, except where contra-indicated by a known etiology, the non-toxic character of the anthracite residue and apparent absence of side effects permits the veterinarian to try this medicament in arthritis of unknown etiology or where the etiology is uncertain, but is not an etiology which contraindicates its use.

Test results to date indicate that medication with the anthracite coal residue constitutes a beneficial treatment for osteoarthritis and osteoarthrosis (primary and secondary) in the canine and equine. As many as 70% of the test animals exhibited a clearly discernable improvement in their symptomatology.

According to one mode of practice of the invention, the anthracite ignition residue is encapsulated in, for example, the gelatin capsules commonly employed for pharmaceuticals, with each capsule containing 50 to 5000 milligrams of the finely divided (e.g., 200 mesh and finer) ignition residue. The capsules are simply administered orally. One exemplary regimen for canines suffering from osteoarthritis or osteoarthrosis is administration of one capsule daily (200 mg) to dogs weighing up to 25 pounds and two capsules daily to larger dogs for a three day period.

An alternative mode of administration, and one better suited to domestic animals than to humans, is administration of the ignition residue in an admixture with food. For example, the anthracite coal ignition residue can be incorporated in a dog food preparation in the proper proportions for a large dog, say 400 mg of residue in a 16 oz. can of prepared dog food.

Repeated allusion to canine has been made in the above discussions of this invention. That is because osteoarthritis and osteoarthrosis is very common among elderly canines, e.g., older than five years of age. An elderly, partially crippled dog will, of course, make the owner of the pet anxiously concerned. Canine treatment constitutes one of the major uses for the composition. Administration of 200 mg/25 lbs. of body weight for three days relieves the crippling symptoms of osteoarthritis and osteoarthrosis in the canine for a great percentage of the treated animals. Since the composition appears to have no serious side effects, and in fact no side effects have as yet been observed, repeat treatment can be made should symptoms of osteoarthritis and osteoarthrosis recur. In some animals, only temporary and partial remission occurs, and treatment at a dosage rate of 50 –100 mg/25 lbs. of body weight daily for a week or more may be advisable.

Some allusion has been made to equines. Horses, particularly race horses, commonly suffer with arthritic ailments of a non-infectious etiology consistent with medication by the anthracite coal residue.

Test studies made on osteoarthritic - osteoarthrotic canines (the three 5-day 200mg/25 lbs. regimen) have demonstrated that the anthracite coal residue has a beneficial effect. In at least 70% of the arthritic dogs treated with the composition of the present invention, substantial remission was observed. Even the 30% failure rate was not absolute. Several of the animals showed visible improvement for brief periods of time. The distinction made in the test studies between successful treatment and failure was arbitrarily taken as essentially complete remission of the symptoms of osteoarthritis or osteoarthrosis for a post medication period in excess of three weeks. In some of the partial failure animals, long term (30 days or more) medication at 50mg/25 lbs. in their food/day caused some remission symptoms.

A limited number of test studies have been made on arthritic race horses. Results demonstrated that the anthracite coal residue had a beneficial effect on 70% of the horses treated. The medication was on the basis of a five to seven day regimen of 5000 mg/day.

The high evidence of osteoarthritis and osteoarthrosis in the canine and equine makes a 70% remission rate gratifying. This rate compares fvorably with heretofore standard medicaments such as aspirin, butazolidine, and anti-inflammatory steroids. At the very least, this remission rate suggests usage of the anthracite coal ignition residue for alternate therapy when side effects dictate withdrawal of the other medicaments.

Animal test studies, i.e., canine and rat, have indicated a tolerance for the anthracite coal ignition residue of the present invention far in excess of 100 mg per kg of body weight. Also, a long term daily treatment schedule (120 days) at a daily dosage of 80mg/kg in rats caused no noticeable side effects nor did it interfere with normal bodily functions including pregnancy, parturation and suckling of young. Pathologic examination was made of blood and tissue sections taken from sacrificed animals, including heart, lungs, spleen, liver, stomach, kidneys, urinary bladder, adrenals, testicles, ovaries, uterus and striated muscle; all tissues appeared normal.

What is claimed is:

1. An anti-arthritic preparation essentially consisting of the ignition residue of anthracite coal in finely divided form, encapsulated in effective dosage unit capsules not exceeding about 5,000 mg/capsule.

2. An anti-arthritic preparation essentially consisting of the ignition residue of anthracite coal compressed into an effective dosage unit bolus form not exceeding about 5,000 mg/dosage unit.

3. An anti-arthritic preparation essentially consisting of the ignition residue of anthracite coal in finely divided form in intimate admixture with a prepared animal food at a daily effective dosage rate not exceeding about 100 mg/kg of the body weight of the animal consuming the food.

4. The anti-arthritic preparation of claim 1 which analyzes as follows: 42–48% $SiO_2$, 5–8% $Fe_2O$, 0.75–1.0% $MgO$, 1.0–1.5% $K_2O$, 0.05–0.10% $ZnO$, 30–35% $Al_2O_3$, 0.75–1.25% $CaO$, 1.0–1.25% $Na_2O$, 0.2–0.4% $CuO$, 0.03–0.1% $Li_2O$, 0.2–0.4% $P_2O_5$, 2.0–3.5 total Carbon, and 3.0–4.0 $H_2O$.

5. The anti-arthritic preparation of claim 1 wherein the ignition residue is from the anthracite sub-group of anthracite coals.

6. A method for treating arthritis which comprises administering orally a finely divided ignition residue of anthracite coal in daily effective dosage units not exceeding about 100 mg/kg of the body weight of the recipient.

7. The method of claim 6 which comprises administering the residue in capsule form.

8. The method of claim 6 which comprises administering the residue in bolus form.

9. The method of claim 6 which comprises administering the residue in intimate admixture with a prepared animal food.

* * * * *